US009650660B2

(12) United States Patent
Seo et al.

(10) Patent No.: US 9,650,660 B2
(45) Date of Patent: May 16, 2017

(54) METHOD FOR SENSITIVELY AND SELECTIVELY SENSING AVIAN INFLUENZA VIRUS USING TERAHERTZ ELECTROMAGNETIC WAVES AND DEVICE USED THEREFOR

(71) Applicant: KOREA INSTITUTE OF SCIENCE AND TECHNOLOGY, Seoul (KR)

(72) Inventors: Min-Ah Seo, Seoul (KR); Dong-Kyu Lee, Seoul (KR); Jun-Seok Lee, Seoul (KR); Jae-Hun Kim, Seoul (KR); Chul-Ki Kim, Seoul (KR); Taik-Jin Lee, Seoul (KR); Seok Lee, Seoul (KR); Young-Min Jhon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/084,925

(22) Filed: Mar. 30, 2016

(65) Prior Publication Data

US 2017/0081695 A1    Mar. 23, 2017

(30) Foreign Application Priority Data

Sep. 23, 2015   (KR) ......................... 10-2015-0134859

(51) Int. Cl.
*G01N 33/569*        (2006.01)
*C12Q 1/02*          (2006.01)
(Continued)

(52) U.S. Cl.
CPC ............. *C12Q 1/02* (2013.01); *G01N 21/59* (2013.01); *G01N 33/56983* (2013.01); *G01N 21/63* (2013.01); *G01N 2333/11* (2013.01)

(58) Field of Classification Search
CPC ................ G01N 33/48; G01N 33/569; G01N 33/56983; G01N 21/01; G01N 21/03;
(Continued)

(56) References Cited

U.S. PATENT DOCUMENTS

2007/0165295 A1* 7/2007 Kim ...................... G02B 5/204
                                                  359/245

FOREIGN PATENT DOCUMENTS

KR    10-2013-0116609 A    10/2013

OTHER PUBLICATIONS

Lee et al. Scientific Reports, vol. 5:15459, pp. 1-7.*
(Continued)

*Primary Examiner* — Maureen Wallenhorst
(74) *Attorney, Agent, or Firm* — Goldilocks Zone IP Law

(57) ABSTRACT

Disclosed herein are a method and device for sensing avian influenza viruses, using terahertz electromagnetic waves. By the method, even a trace amount of avian influenza viruses in a liquid state can be accurately discriminated and sensed, with high sensitivity and selectivity, using a sensing chip that works in a terahertz electromagnetic wave band. Using the method, avian influenza viruses even at low concentrations can be accurately analyzed with high sensitivity and selectivity in which terahertz electromagnetic waves are irradiated onto avian influenza viruses through a sensing chip having a meta unit in which a pattern is formed to amplify a frequency corresponding to an absorption frequency of an avian influenza virus of interest.

6 Claims, 3 Drawing Sheets

(51) Int. Cl.
*G01N 21/59* (2006.01)
*G01N 21/63* (2006.01)

(58) Field of Classification Search
CPC .... G01N 21/63; G01N 21/59; G01N 2333/11; C12Q 1/02
USPC .......... 436/63, 164, 165, 171; 435/5, 235.1, 435/239; 422/82.05, 82.09
See application file for complete search history.

(56) References Cited

OTHER PUBLICATIONS

Reinhard et al. Proceedings of SPIE (Terahertz and Ultrashort Electromagnetic Pulses for Biomedical Applications), vol. 8585, 858507, 2013, pp. 1-11.*
Park et al. Detection of microorganisms using terahertz metamaterials, Scientific Reports, May 16, 2014, pp. 1-7.
Hu Tao et al.A metamaterial absorber for the terahertz regime: Design, fabrication and characterization, Optics Express, May 12, 2008, pp. 7181-7188, vol. 16, No. 10.
Office Action from Korean Intellectual Property Office, mailed on Sep. 9, 2016, which is a corresponding Korean patent application No. 10-2015-0134859 of present application.

\* cited by examiner

FIG. 3

METHOD FOR SENSITIVELY AND SELECTIVELY SENSING AVIAN INFLUENZA VIRUS USING TERAHERTZ ELECTROMAGNETIC WAVES AND DEVICE USED THEREFOR

CROSS REFERENCE TO RELATED APPLICATION

The present application claims the benefit of Korean Patent Application No. 10-2015-0134859 filed on Sep. 23, 2015.

BACKGROUND OF THE INVENTION

1. Field of the Invention

The present disclosure relates to a method and device for sensing avian influenza viruses, using terahertz electromagnetic waves. Particularly, the present disclosure relates to a method by which even a trace amount of avian influenza viruses in a liquid state can be accurately detected and discriminated, with high sensitivity and selectivity, using a sensing chip that works in a terahertz electromagnetic wave band, and to a device therefor. Also, the present disclosure relates to a method for sensitively and selectively sensing avian influenza viruses even at low concentrations, in which terahertz electromagnetic waves are irradiated onto avian influenza viruses through a sensing chip having a meta unit in which a pattern is formed to amplify a frequency corresponding to an absorption frequency of an avian influenza virus of interest, thus allowing for the quantitative analysis of avian influenza viruses, and a device therefor.

2. Description of the Related Art

Recently, outbreaks of avian influenza have been occurring with increasing frequency. For prevention of the outbreak and damage caused by avian influenza, it is very important to determine virus subtypes responsible for currently epidemic avian influenza viruses in an early stage.

However, there is a variety of subtypes of avian influenza viruses, and base sequencing of the RNA gene of the currently working influenza virus by gene inspection as described in the following patent document is prerequisite for the determination of the subtype of a currently working avian influenza virus.

PATENT DOCUMENT

Korean Patent Unexamined Application Publication No. 10-2013-0116609 (issued Oct. 24, 2013) "Probes and DNA chip for subtyping avian influenza viruses and method for detecting avian influenza viruses using the same"

However, the method has difficulty in determining the subtype of avian influenza virus in an early stage, and requires much time and cost because a large number of biological samples are necessary for infection determination.

Accordingly, there is an urgent need for a method for rapidly specifying subtypes of avian influenza viruses by primary screening before the determination of the subtype, and a technique by which precise avian influenza virus subtypes can be rapidly detected and discriminated even at a concentration as low as in an actual blood condition.

SUMMARY OF THE INVENTION

Accordingly, the present invention has been made keeping in mind the above problems occurring in the related art, and an object of the present disclosure is to provide a method by which even a trace amount of avian influenza virus in a liquid state can be accurately detected and discriminated for virus subtypes, with high sensitivity and selectivity, using a sensing chip that works in a terahertz electromagnetic wave band, and a device therefor.

Another object of the present disclosure is to provide a method for accurately analyzing avian influenza viruses by measuring changes in transmittance and frequency shift of the light reflected from the target avian influenza viruses through a sensing chip, and a device therefor.

In order to accomplish the above objects, a method and a device for sensitively and selectively sensing avian influenza virus using terahertz electromagnetic waves, have the following constitutions.

An aspect of the present disclosure provides a method for sensitively and selectively sensing avian influenza virus, using a sensing chip, wherein the sensing chip has a meta unit in which a pattern is formed for amplifying a frequency corresponding to an absorption frequency of an avian influenza virus of interest, and wherein the sensing chip, when irradiated with terahertz electromagnetic waves, passes the waves therethrough to the avian influenza virus of interest and amplifies waves reflected from the avian influenza virus of interest, whereby the avian influenza virus of interest can be analyzed for subtype even when it is present at a low concentration.

In some embodiments, the method comprises: a target disposition step in which an avian influenza virus of interest is disposed on a sensing chip having a meta unit in which a pattern is formed for amplifying a frequency corresponding to an absorption frequency of an avian influenza virus of interest; a light irradiation step in which terahertz electromagnetic waves are irradiated to the avian influenza virus of interest on the meta unit; and a virus determination step in which the terahertz electromagnetic waves passing through the sensing chip are measured for transmittance or frequency change to specify the avian influenza virus.

In a particular embodiment, the virus determination step may be adapted to measure the terahertz electromagnetic waves passing through the meta unit for transmittance or frequency change thus to specify avian influenza viruses and to determine concentrations of the specified avian influenza viruses, based on the fact that transmittance or a frequency change is elevated when the absorption frequency of a target avian influenza virus corresponds to the resonant transmission frequency of the meta unit.

In a particular embodiment, the method may further comprise: a quantitative analysis step in which the avian influenza virus of interest is quantitatively analyzed, based on a change in the transmittance and/or frequency of the terawave passing through the sensing chip with a concentration of the avian influenza virus of interest.

In a particular embodiment, the pattern may be in a form of slits, each ranging in width from 10 nm to 1 µm, in thickness from 100 nm to 1 µm, and in length from 10 µm to 1 mm.

In a particular embodiment, the pattern may be an array of slits that is formed at regular gaps in the meta unit.

In accordance with another aspect thereof, the present disclosure provides a device for sensing avian influenza viruses, using the sensing chip used in the method of claim 6.

BRIEF DESCRIPTION OF THE DRAWINGS

The above and other objects, features and other advantages of the present invention will be more clearly under

FIG. 3 is a graph showing measurement results of avian influenza virus subtype H9N2 obtained by using the sensing method of FIG. 1.

DESCRIPTION OF THE PREFERRED EMBODIMENTS

Below, a description will be given of some embodiments of the present invention in conjunction with the accompanying drawings. Unless otherwise defined, the meaning of all terms including technical and scientific terms used herein is the same as that commonly understood by one of ordinary skill in the art to which the present invention belongs. It will be further understood that terms, such as those defined in commonly used dictionaries, should be interpreted as having a meaning which is consistent with their meaning in the context of the relevant art and the present disclosure, and will not be interpreted in an idealized or overly formal sense unless expressly so defined herein. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present disclosure, the description thereof will be omitted. Unless the context clearly requires otherwise, throughout the description and the claims, the words "comprise", "comprising", and the like are to be construed in an inclusive sense as opposed to an exclusive or exhaustive sense, that is to say, in the sense of "including, but not limited to".

Figure 1:
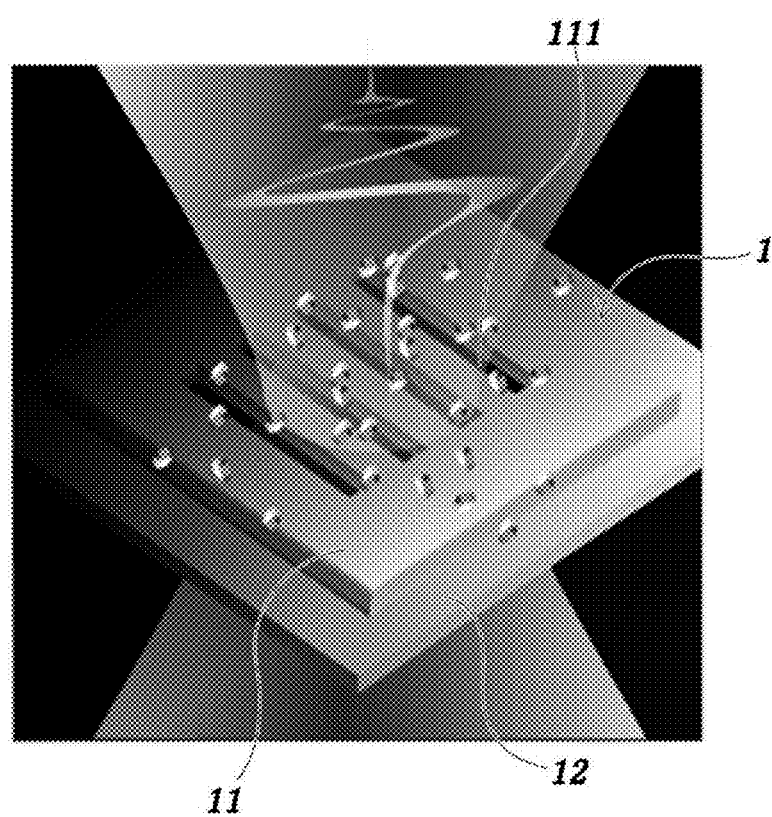
- FIG. 1 is a view illustrating a method for sensing avian influenza viruses in accordance with an embodiment of the present disclosure.

The present disclosure addresses a method for sensitively and selectively sensing avian influenza viruses using terahertz electromagnetic waves. The method is described in detail with reference to FIGS. 1 to 3. The method is adapted to accurately analyze avian influenza viruses in a liquid state even at low concentrations, with high sensitivity and selectivity, in which terahertz electromagnetic waves (hereinafter referred to as "terawaves") are irradiated onto avian influenza viruses through a sensing chip 1 having a meta unit 11 in which a pattern is formed to amplify a frequency corresponding to an absorption frequency of an avian influenza virus of interest.

As described above, it is very difficult to discriminate subtypes of avian influenza viruses and to measure concentrations of avian influenza viruses. In the present disclosure, a sensing chip 1 having a meta unit 11 in which patterns are formed to amplify an absorption frequency of avian influenza viruses of interest by subtype is used to irradiate terawaves onto avian influenza viruses in respective trace amounts (or low concentrations) and to determine the subtype of the avian influenza virus of interest and to measure the concentration of the avian influenza virus of interest. There are many subtypes of avian influenza viruses according to combinations of H and N subtypes, and avian influenza viruses show respective characteristic absorption spectra in a terahertz frequency band, with respective absorption peaks at different frequencies. In this regard, a meta unit is designed such that it transmits terawaves and amplifies a frequency corresponding to the characteristic absorption frequency in response to a specific avian influenza virus subtype of interest. Based on this principle, a target biological sample in a liquid state can be selectively specified for subtypes among various avian influenza viruses, and can be quantitatively analyzed even at a low concentration.

Now, a description will be given of a device useful in the method for sensing avian influenza viruses. The device comprises a sensing chip 1 having a meta unit 11 that works in a terawave range, an irradiator (not shown) for irradiating terawaves onto the sensing chip 1, a detector (not shown) for measuring a transmittance and/or a frequency change of the terawaves passing through the sensing chip 1 to specify a subtype of the avian influenza virus and to determine concentrations of the specified avian influenza virus.

The sensing chip 1 is configured to work in a terawave range, and comprises a meta unit 11 in which a pattern is formed to selectively amplify a frequency of interest, and a transparent substrate 12 for supporting the meta unit 11.

Figure 2:
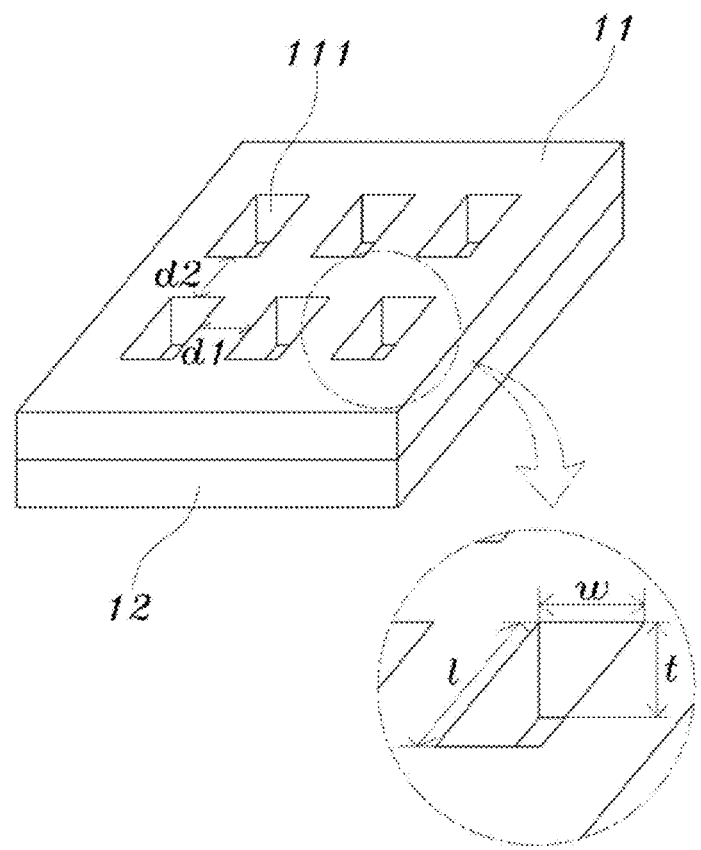
FIG. 2 is a perspective view of a sensing chip used in a method for sensing avian influenza viruses in accordance with an embodiment of the present disclosure.

The meta unit 11 is configured to have a pattern 111 for selectively amplifying a frequency of interest. For example, the pattern 111 may be an array of slits that is formed at regular gaps in the meta unit, each penetrating through the meta unit, as shown in FIG. 2. The meta unit 11 may be preferably made of a metallic material, such as gold, silver, copper, aluminum, etc. In the pattern 111, the slits are constant in shape, size, and gap (hereinafter referred to as "spec"). Preferably, the slits range in width from (w) 10 nm to 1 um, in thickness (t) from 100 nm to 1 um, and in length (l) from 10 um to 1 mm, with gaps of 1 nm to 1 mm therebetween in both the widthwise direction (d1) and the lengthwise direction (d2). The sensing chip 1 may be designed to amplify a specific frequency by adjusting the material of the meta unit 11 and/or the spec of the pattern 111 to set the resonance transmission frequencies of the sensing chip 1. Concrete examples are described, below.

In a particular embodiment of the present disclosure, the substrate 12, positioned beneath one side of the meta unit 11 to support the meta unit 11, is made of a transparent material, such as quartz, silicon, sapphire, glass, etc.

The irradiator irradiates onto the sensing chip 1 terahertz electromagnetic waves with a frequency of, for example, 0.1 to 5 THz. The detector is provided for measuring a transmittance and/or a frequency change of the terawaves passing through the sensing chip 1 to specify subtypes of avian influenza viruses and to determine concentrations of the specified avian influenza viruses. After a sample is loaded on the meta unit 11 of the sensing chip 1, terawaves are irradiated from the irradiator onto the sensing chip 1, and the detector measures the transmittance or frequency change of the terawaves passing through the sensing chip 1 to specify subtypes of avian influenza viruses and to determine concentrations of the specified avian influenza viruses.

Turning now to the method for sensing avian influenza viruses using the device described above, it comprises a target disposition step in which an avian influenza virus of interest is distributed on a sensing chip 1 having a meta unit 11 in which a pattern is formed for selectively amplifying a specific frequency, a light irradiation step in which terahertz electromagnetic waves are irradiated to the avian influenza virus of interest on the meta unit 11, and an avian influenza virus determination step in which the terahertz electromagnetic waves passing through the sensing chip 1 are measured for transmittance or frequency change to specify avian influenza viruses and to determine concentrations of the specified avian influenza viruses.

The target disposition step is a step in which an avian influenza virus of interest (sample) is distributed on the sensing chip 1 having the meta unit 11 in which a pattern is formed for selectively amplifying a specific frequency. The avian influenza virus to be analyzed is distributed on the meta unit 11 of the sensing chip 1 through which a resonant transmission frequency corresponding to the absorption frequency of a subtype of avian influenza virus of interest is emitted. In the target disposition step, for example, if H9N2 avian influenza virus is a target, a sample is placed on the meta unit 11 of the sensing chip 1 from which a resonant transmission frequency identical or corresponding to the absorption frequency of avian influenza virus subtype H9N2 is emitted. In the target disposition step, samples are placed on sensing chips 1 that are respectively designed according to avian influenza virus subtypes to be analyzed.

In the light irradiation step, terahertz electromagnetic waves are irradiated onto an avian influenza virus of interest (sample) on the meta unit 11. In this regard, the irradiator emits a terawave with a frequency of 0.1 to 3 THz.

In the virus determination step, the terahertz electromagnetic waves passing through the sensing chip 1 are measured for transmittance or frequency change to specify a subtype of avian influenza virus. Based on the fact that transmittance or frequency change is elevated when the absorption frequency of a target avian influenza virus corresponds to the resonant transmission frequency of the meta unit, the subtype of avian influenza virus can be determined. By way of example, on the assumption that avian influenza virus subtype H5N2 is present in a sample, a sensing chip manufactured to emit a resonant transmission frequency corresponding to the absorption frequency of avian influenza virus subtype H5N2 may be employed to detect a large change in the transmittance and/or frequency of the terawave (change to a predetermined degree or more). When avian influenza virus subtype H1N1 is present in a sample, the sensing chip designed to emit a resonant transmission frequency corresponding to the absorption frequency of avian influenza virus subtype H5N2 can detect a small change in the transmittance and/or frequency of the terawave (change less than a predetermined degree). The subtype of avian influenza virus can thus be specified in consideration of the change in the transmittance and/or frequency of the terawave passing the sensing chip 1.

Figure 3:
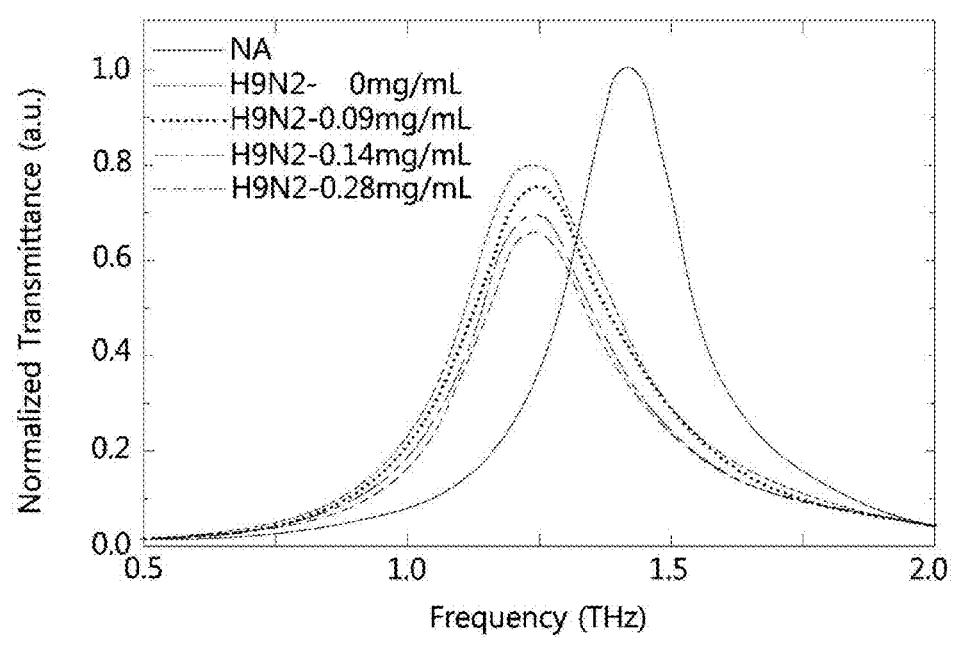

In another embodiment of the present disclosure, the method may further comprise a quantitative analysis step in which the avian influenza virus of interest is quantitatively analyzed, based on a change in the transmittance and/or frequency of the terawave passing through the sensing chip with the concentration of the avian influenza virus of interest. Because the transmittance and frequency vary with the concentration of an avian influenza virus of interest, the magnitude of the transmittance and frequency shift of the terawave detected from the sensing chip allows for determining and providing the quantitative data of the avian influenza virus of interest. Accordingly, the method may be used as an index for new quantitative analysis of viral samples that are difficult to quantitatively analyze. For instance, a sensing chip (substrate made of silicon 500 μm thick, a meta unit made of gold 130 nm thick, and a pattern 500 nm wide, 40 μm long, and 130 nm thick) was manufactured to emit a resonant transmission frequency corresponding to the absorption frequency of avian influenza virus subtype H9N2, and one drop of a sample (comprising a buffer (PBS) and 0, 0.09, 0.14, or 0.28 mg/mℓ avian influenza virus subtype H9N2) was added onto the meta unit 11 of the sensing chip 1. Then, terawaves were irradiated onto the sample, followed by measuring the transmittance and frequency change of the terawaves passing through the sensing chip 1. The measurement results are depicted in FIG. 3 (in which NA accounts for terawaves that were irradiated onto the sensing chip 1 with no samples placed on the chip). As can be seen in FIG. 3, the transmittance and the frequency vary with the concentration of avian influenza virus. Thus, the magnitude of the transmittance and frequency shift of the terawave detected from the sensing chip allows for the quantitative analysis of avian influenza virus.

As described in the foregoing embodiments and constitutional elements of the present disclosure, and their combinations, the present invention enjoys the following advantages.

The method and device according to the present invention can rapidly sense an avian influenza virus subtype, with high sensitivity and selectivity, using terahertz electromagnetic waves, even though a trace amount of a virus sample in a liquid state is present.

Also, capable of determining the concentration of avian influenza virus in response to the magnitude of the transmittance and frequency change of the light detected through the sensing chip, the method and device according to the present invention can find applications in the quantitative analysis of avian influenza viruses.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for sensing avian influenza virus in a sample, using a sensing chip, comprising:
    applying the sample to a meta unit of the sensing chip, wherein the meta unit includes a pattern in a form of slits that serves to amplify a frequency corresponding to an absorption frequency of an avian influenza virus of interest;
    irradiating light in a form of terahertz electromagnetic waves to the sample on the meta unit of the sensing chip; and
    measuring the terahertz electromagnetic waves reflected from the avian influenza virus in the sample by measuring transmittance or frequency change of the terahertz electromagnetic waves to detect a subtype of the avian influenza virus.

2. The method of claim 1, wherein the method comprises:
    a target disposition step in which an avian influenza virus of interest is disposed on the sensing chip having a meta unit in which a pattern is formed for amplifying a frequency corresponding to an absorption frequency of an avian influenza virus of interest;
    a light irradiation step in which terahertz electromagnetic waves are irradiated to the avian influenza virus of interest on the meta unit; and
    a virus determination step in which the terahertz electromagnetic waves passing through the sensing chip are measured for transmittance or frequency change to specify the avian influenza virus.

3. The method of claim 2, wherein the virus determination step to measure the terahertz electromagnetic waves passing through the meta unit for transmittance or frequency change thus to specify avian influenza viruses and to determine concentrations of the specified avian influenza viruses, based on the fact that transmittance or a frequency change is elevated when the absorption frequency of a target avian influenza virus corresponds to a resonant transmission frequency of the meta unit.

4. The method of claim 2, further comprising:
a quantitative analysis step in which the avian influenza virus of interest is quantitatively analyzed, based on a change of the transmittance and/or frequency of the terahertz electromagnetic waves passing through the sensing chip with a concentration of the avian influenza virus of interest.

5. The method of claim 2, wherein the pattern is in a form of slits, each ranging in width from 10 nm to 1 μm, in thickness from 100 nm to 1 μm, and in length from 10 μm to 1 mm.

6. The method of claim 5, wherein the pattern is an array of slits that is formed at regular gaps in the meta unit of 1 nm to 1 mm in a widthwise direction and 1 nm to 1 mm in a lengthwise direction.

* * * * *